(12) United States Patent
Khalaj

(10) Patent No.: US 11,672,899 B2
(45) Date of Patent: Jun. 13, 2023

(54) DEVICE AND METHOD FOR RESIZING ADIPOSE TISSUE FOR IMPLANTATION

(71) Applicant: HEALEON LLC, Solana Beach, CA (US)

(72) Inventor: Ben M. Khalaj, Irvine, CA (US)

(73) Assignee: Healeon LLC, Solana Beach, CA (US)

( * ) Notice: Subject to any disclaimer, the term of this patent is extended or adjusted under 35 U.S.C. 154(b) by 0 days.

(21) Appl. No.: 16/520,653

(22) Filed: Jul. 24, 2019

(65) Prior Publication Data

US 2020/0061258 A1 Feb. 27, 2020

Related U.S. Application Data

(60) Provisional application No. 62/702,614, filed on Jul. 24, 2018.

(51) Int. Cl.
| | |
|---|---|
| B26D 3/18 | (2006.01) |
| A61M 1/00 | (2006.01) |
| B26D 1/03 | (2006.01) |
| B26D 3/28 | (2006.01) |
| B26D 7/06 | (2006.01) |
| B26D 11/00 | (2006.01) |
| C12M 1/33 | (2006.01) |
| A61L 27/36 | (2006.01) |

(52) U.S. Cl.
CPC ............. *A61M 1/892* (2021.05); *B26D 1/03* (2013.01); *B26D 3/185* (2013.01); *B26D 3/28* (2013.01); *B26D 7/0658* (2013.01); *B26D 11/00* (2013.01); *C12M 45/02* (2013.01); *A61L 27/3691* (2013.01); *A61M 1/895* (2021.05); *A61M 2202/08* (2013.01); *B26D 2011/005* (2013.01)

(58) Field of Classification Search
CPC ........ B26D 1/03; B26D 7/0658; B26D 11/00; B26D 2011/005; B26D 3/185
USPC ............................... 83/402, 857, 955
See application file for complete search history.

(56) References Cited

U.S. PATENT DOCUMENTS

| | | | |
|---|---|---|---|
| 3,298,411 A | | 1/1967 | Rosett |
| 3,593,854 A | * | 7/1971 | Swank ............... A61M 5/165 210/326 |

(Continued)

FOREIGN PATENT DOCUMENTS

WO   WO-2004108998 A1 * 12/2004 ............... B26D 1/28

OTHER PUBLICATIONS

WO PCT/US19/43151 ISR and Written Opinion, dated Oct. 22, 2019.

(Continued)

*Primary Examiner* — Kenneth E Peterson
(74) *Attorney, Agent, or Firm* — Fish & Richardson P.C.

(57) ABSTRACT

A deagglomerator for use in resizing masses of cells. The deagglomerator may include a plurality of apertures defined by a plurality of front and back edges. The masses of cells may be passed through the plurality of apertures from the front to the back, and from the back to the front, repeatedly. The deagglomerator may also include a plurality of blades that may aid in the deagglomeration of the cell masses. The deagglomerator may be configured between two syringes so that the tissue may be passed back and forth from the first syringe through the device to the second syringe, and then back again from the second syringe through the device and to the first syringe. In this way, the masses of cells may be properly deagglomerated.

9 Claims, 9 Drawing Sheets

(56) References Cited

U.S. PATENT DOCUMENTS

| | | | | |
|---|---|---|---|---|
| 4,115,277 | A * | 9/1978 | Swank | A61M 1/3627 210/436 |
| 4,372,184 | A * | 2/1983 | Fisher | B26D 3/185 83/402 |
| 4,911,045 | A * | 3/1990 | Mendenhall | B26D 3/24 83/402 |
| 5,804,366 | A | 9/1998 | Hu et al. | |
| 6,020,196 | A | 2/2000 | Hu et al. | |
| 6,871,673 | B2 * | 3/2005 | Crittenden | B23D 35/002 83/955 |
| 7,025,880 | B2 * | 4/2006 | Lamb | B01D 29/03 15/264 |
| 9,943,978 | B2 * | 4/2018 | Walker | B26D 7/0658 |
| 2004/0018575 | A1 * | 1/2004 | Rappin et al. | G01N 1/286 435/7.92 |
| 2006/0255191 | A1 * | 11/2006 | Chiang et al. | A61L 11/00 241/23 |
| 2010/0184197 | A1 | 7/2010 | Dong et al. | |
| 2013/0087643 | A1 * | 4/2013 | Tremolada | C12M 45/02 241/24.1 |
| 2013/0109086 | A1 | 5/2013 | Kobayashi et al. | |
| 2013/0123747 | A1 | 5/2013 | Tremolada | |
| 2013/0233141 | A1 * | 9/2013 | Hunt | B26D 3/26 83/167 |
| 2015/0345200 | A1 * | 12/2015 | Repac | B26D 1/30 241/84.3 |
| 2015/0374888 | A1 | 12/2015 | Shippert | |
| 2016/0069781 | A1 * | 3/2016 | Middlebrook et al. | B02C 18/02 241/15 |
| 2016/0333305 | A1 | 11/2016 | Pilkington et al. | |
| 2017/0216744 | A1 | 8/2017 | Kondo et al. | |
| 2018/0154536 | A1 * | 6/2018 | Repac | B26D 3/24 |
| 2018/0348097 | A1 | 12/2018 | Abbott et al. | |

OTHER PUBLICATIONS

International Preliminary Report on Patentability in International Appln. No. PCT/US2019/043151, dated Jan. 26, 2021, 8 pages.

Supplementary European Search Report in European Appln No. 19841885.7, dated Apr. 13, 2022, 8 pages.

* cited by examiner

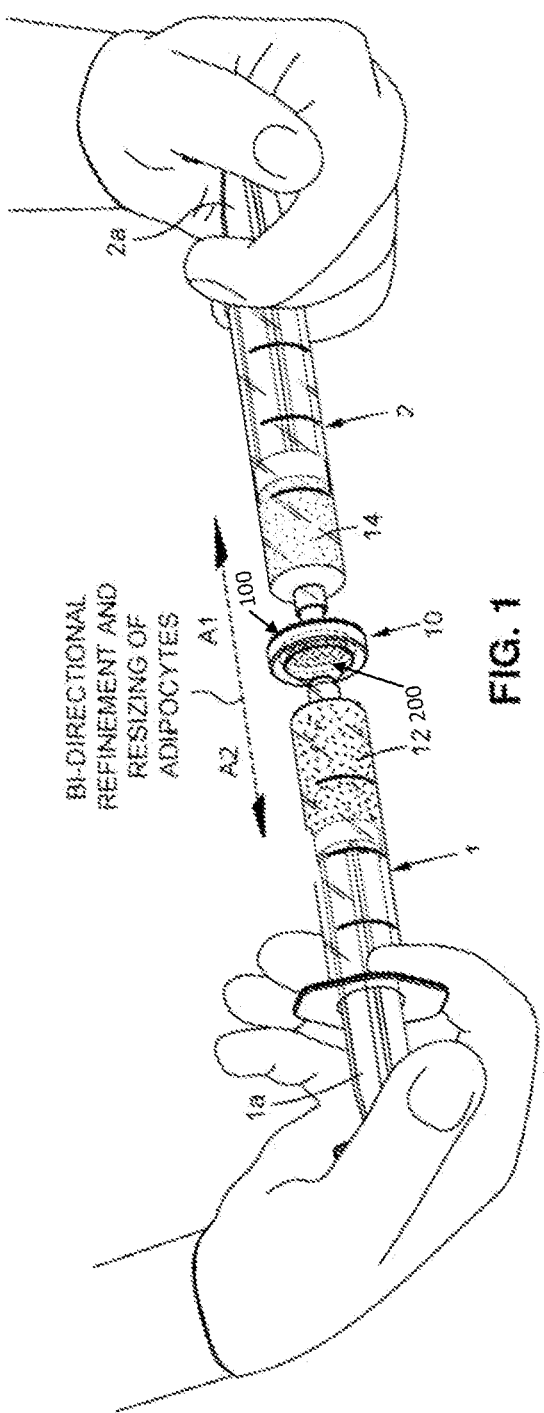
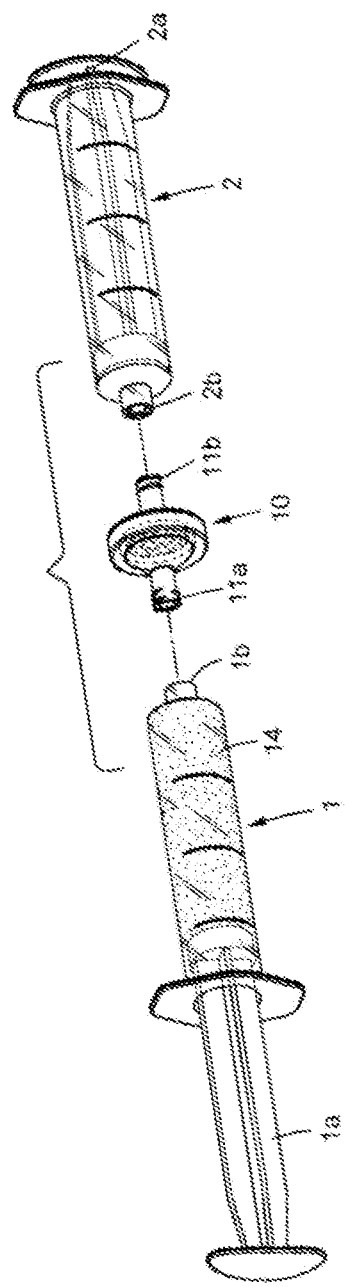
FIG. 1
FIG. 2

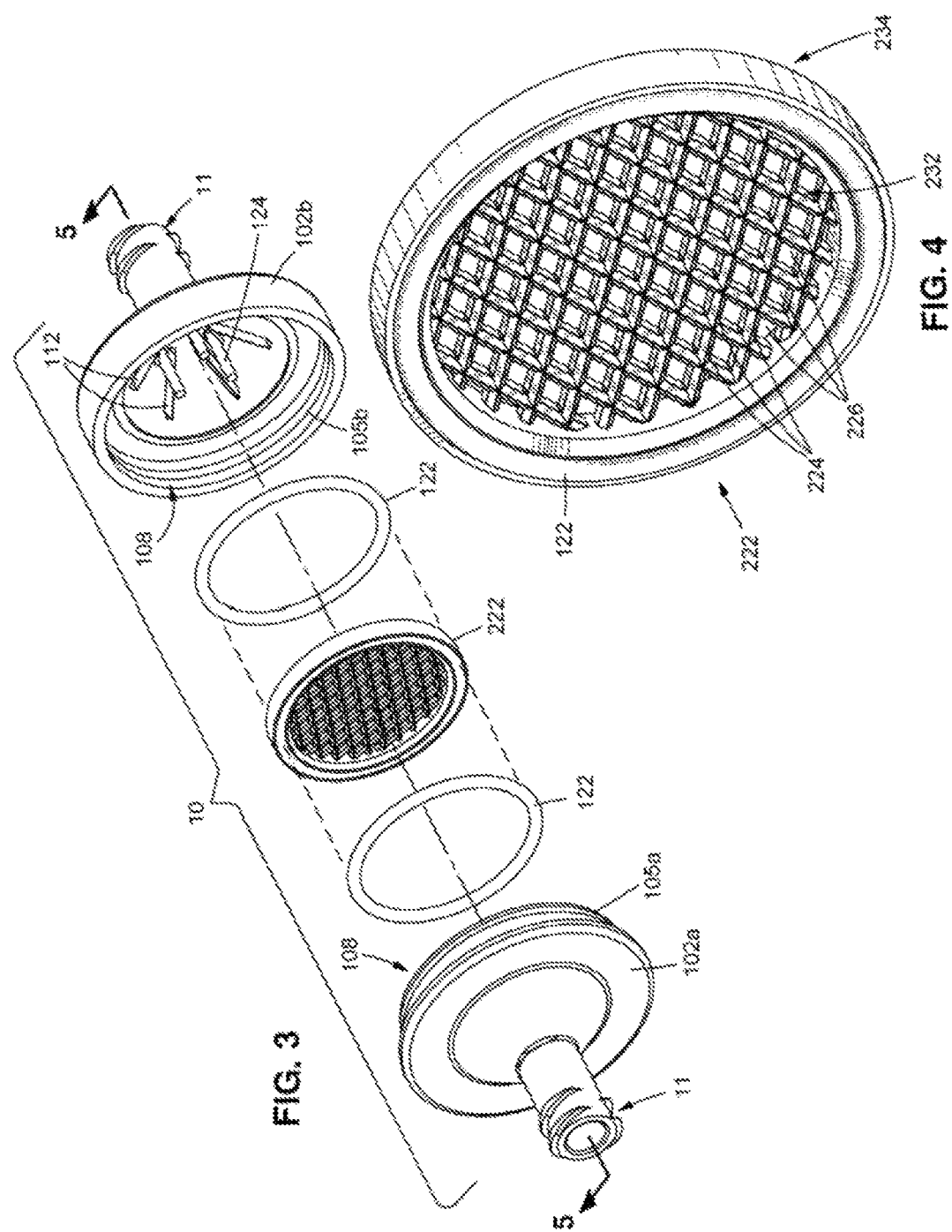

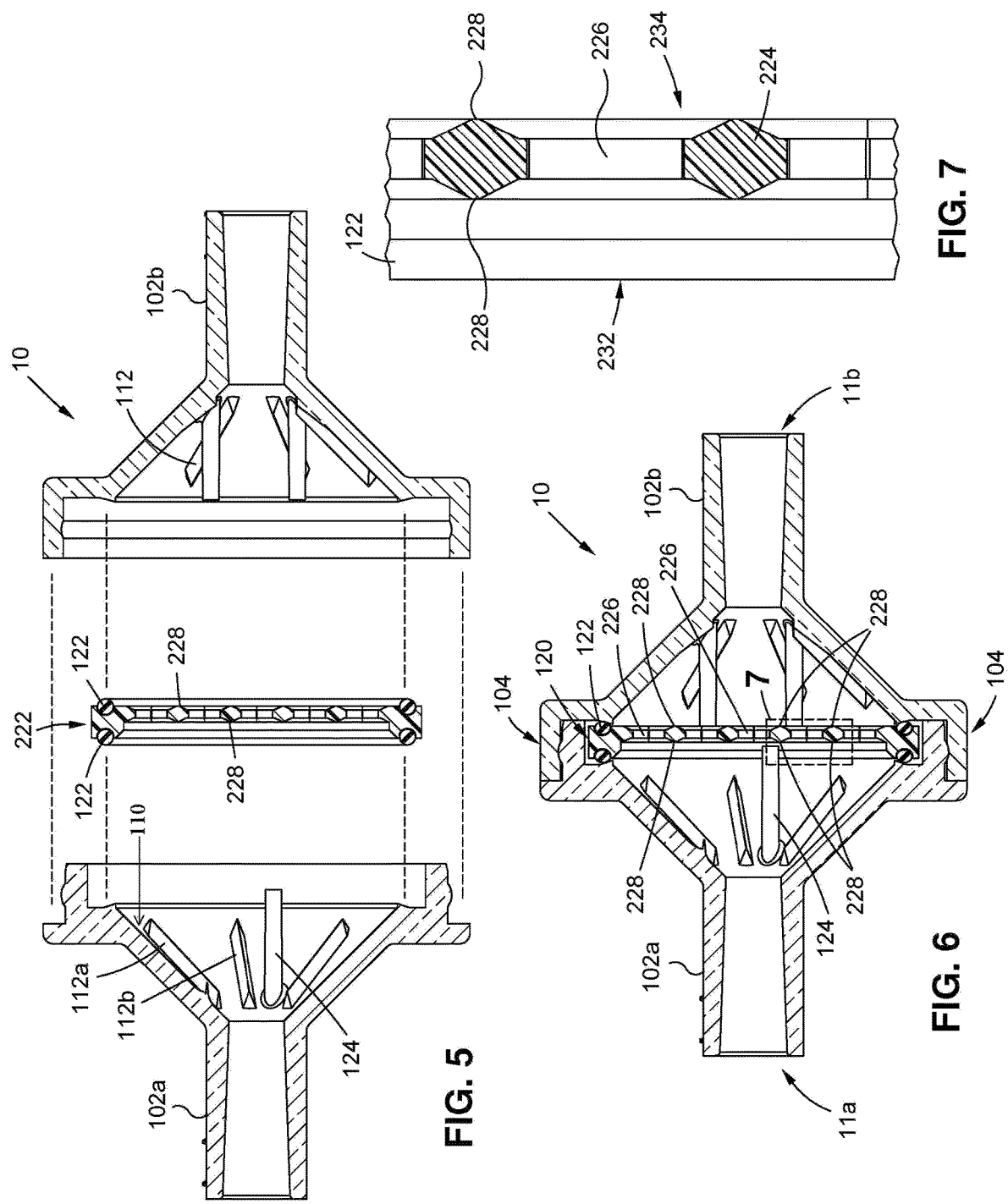

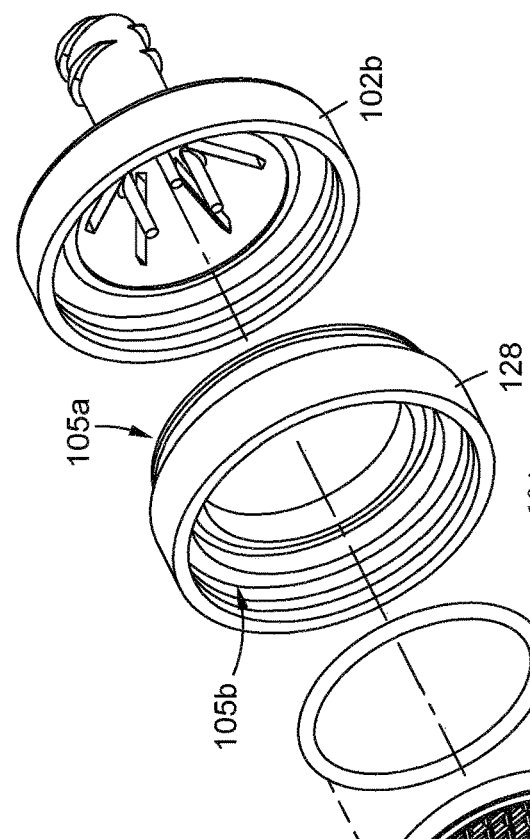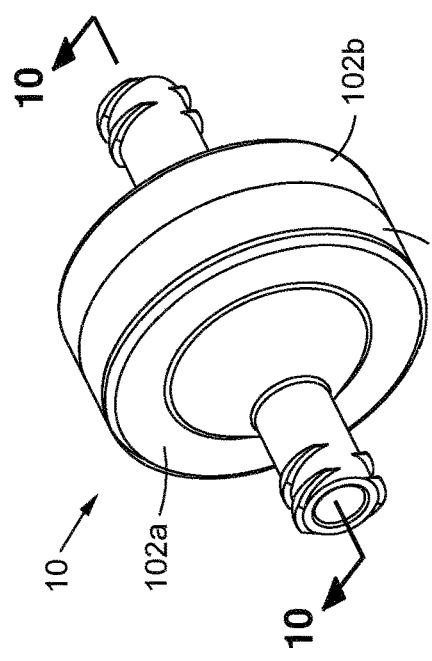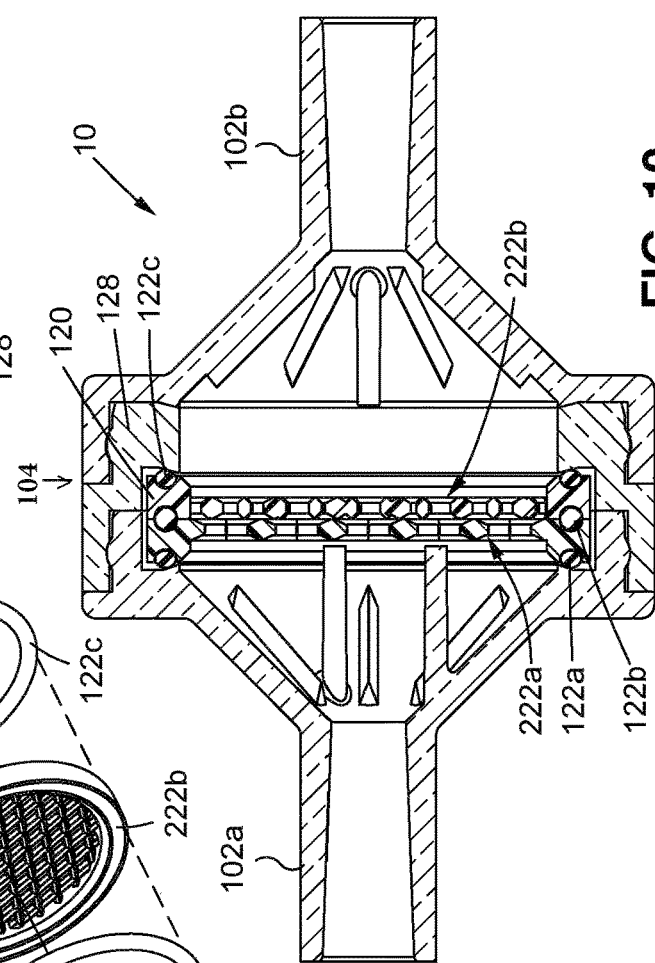

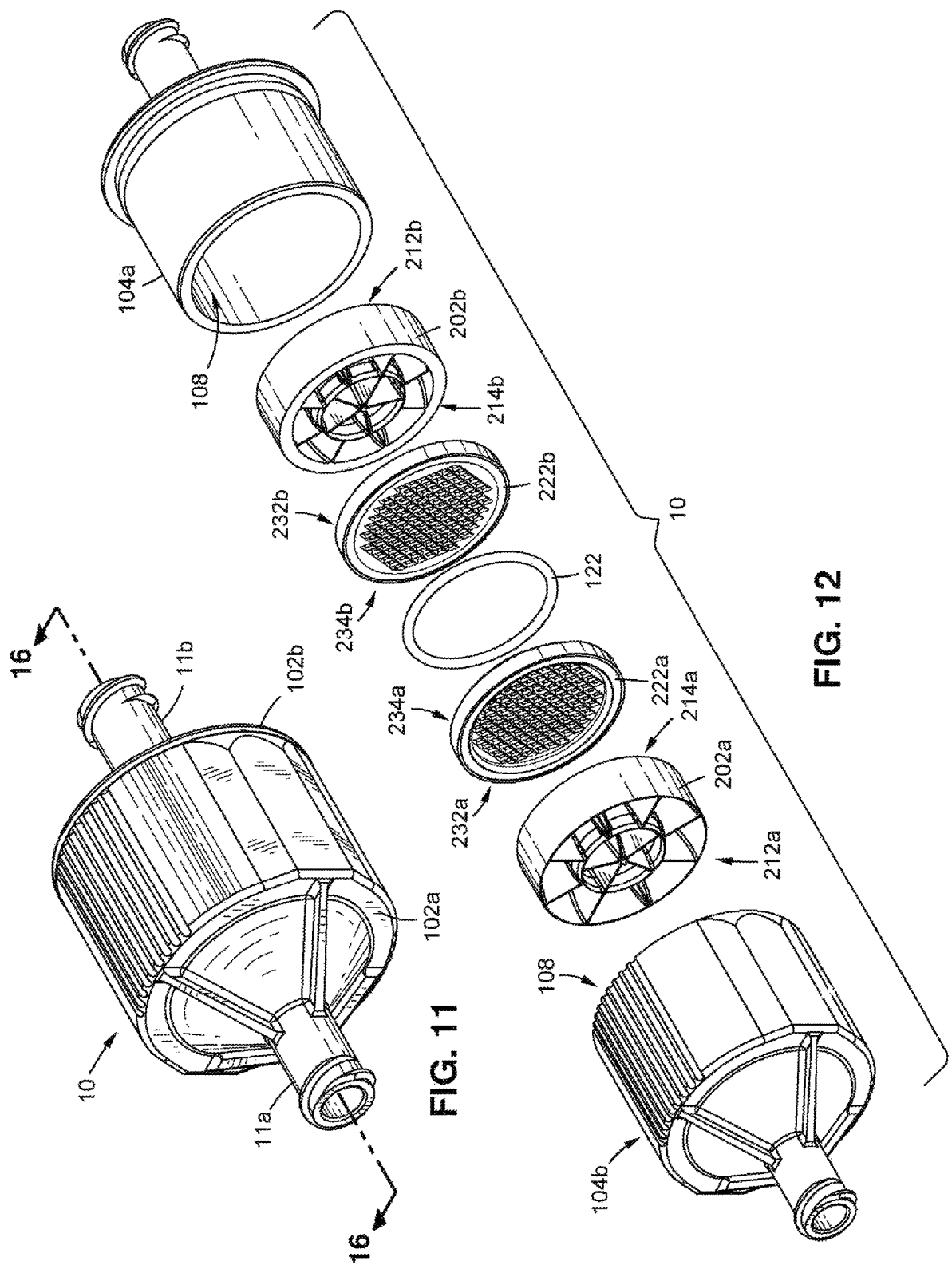

DEVICE AND METHOD FOR RESIZING ADIPOSE TISSUE FOR IMPLANTATION

CROSS-REFERENCE TO RELATED APPLICATIONS

This application claims benefit of U.S. Provisional 62/702,614, filed Jul. 24, 2018, which is hereby incorporated by reference in its entirety.

FIELD

The invention relates to devices, systems and methods of resisting masses of tissue, including the resizing of adipose cell clusters for medical implantation procedures.

BACKGROUND

The following description of the background of the invention is provided simply as an aid in understanding the invention and is not admitted to describe or constitute prior art to the invention.

Fat cells are ideal dermal filler that can be obtained by means of a liposuction procedure which involves extraction of adipose tissue from any donor area of the patient including, for example, subcutaneous hip, abdomen or knee areas, under local anesthesia or generally in outpatient settings. The harvested tissue then may be reinjected into another part of the patient's body (e.g., into the patient's lips, facial wrinkles, etc.). The injected tissue may then, enhance the patient's facial fullness, fill creases and/or build up shallow contours. However, upon initial removal from the patient's body, the adipose tissue may include agglomerated clumps of fat cells that may be too large to be reinjected into the patient. For example, the extracted masses of fat cells may be too large to pass through minimally-invasive thin needles that may be required for certain medical procedures. In addition, larger sized fat cell clusters upon injection into the patient may not interact with the patient's stem cells as well as smaller sized fat, cell clusters.

A broadly accepted method for harvesting adipose tissue for transfer is using the negative pressure syringe technique which involves preparing the area with tumescent solution then using a harvesting cannula attached to 10, 30, or 60 ml syringe. The plunger is pulled back (withdrawn) to create negative pressure when the harvesting cannula is present at the harvesting site within the patient. The cannula is moved within the harvesting site until negative pressure is lost or the syringe is full of lipoaspirate. This aspirate is then either drained excess fluid by either a filter, gravity separation, or centrifugation prior to the being transplanted into the patient.

The Coleman lipostructure technique is a method for processing, the aspirate prior to transplantation. The harvesting syringes containing the lipoaspirate are closed at the bottom by a Luer-lock cap and are centrifuged to separate the liquid phase from the solid biological material. After centrifugation, the anesthetic and biological liquids are manually drained through the uncapped Luer-lock cap. The cell fragments and unbound oil released from lysed and damaged adipocytes are removed only in an incomplete and rudimentary manner.

Although the Coleman and similar techniques are relatively simple and have several advantages, they suffer certain drawbacks. First, the step of suction and separation by centrifugation causes considerable damage and lysis of adipocytes and the concomitant release of oil. This free oil generally is not completely removed and makes a significant portion of the lipoaspirate unusable due to high levels of oil contamination (i.e., the portion of cell material that is located on the upper part of the syringe barrel after centrifugation). The presence of oil in the biological filler increases the risk of infection and rejections and causes increased inflammation. Furthermore, these processes involve multiple contacts of the liposuctioned material with several instruments, as well as a significant exposure to air in a potentially non-sterile environment, further increasing the risk of contamination and, ultimately, infection.

A rarely-used technique for adipocyte processing involves mechanical fragmentation of the suctioned cell agglomerate using a blender separate fat lobules and provide an injectable cell suspension. As with the techniques discussed above, this blender technique suffers similar drawbacks including caused a significant amount of adipocyte damage and lysis, the potential for contamination, and that a significant portion of the harvesting material (as much as 50%) being unsuitable for use in aesthetic procedures. Furthermore, the quantity of usable cell suspension that can be obtained using the above described procedure and devices largely depends on the skill of the health care staff and operational variables including the speed and operating time of the blender and centrifuge. Excessive blade speed and/or poorly maintained cutting blades may not sufficiently separate fat lobule, but instead cause mechanical break of the cell walls of a large amount of adipocytes.

Other processing techniques involve washing the aspirate though a filter or strainer (fine mesh grid). This also has drawbacks. The filter/strainer net may become easily clogged with the harvested material which then requires a manual cleaning or removal of the fat and large cellular agglomerates from the mesh which also increases the risk of contamination and reduces the yield from the aspirated sample.

Accordingly, there is a need for a device, system and method that may resize larger masses of cells (e.g., adipose cells) into smaller sized masses without damaging the individual cells. There is also a need to do so without unnecessarily disallowing larger masses of cells from being resized.

SUMMARY

The present disclosure provides a device and method of use for deagglomerating masses of cells (e.g., masses of adipose cells). The device may be described as a tissue deagglomerator, a tissue sizer, or a fat sizing device.

The device generally comprises a housing assembly and one or more cutting elements contained within the inner volume of that housing assembly. The housing assembly is designed to connect to a first syringe and a second syringe and create a fluid flow path therebetween. In some embodiments, the fluid flow path is substantially linear, as illustrated in the various figures. In some embodiments, the housing assembly connects to the syringes through ports. Optionally, the ports comprise Luer lock connectors of either the threaded or slip-fit design.

In some embodiments, the housing assembly comprises two housing members, wherein each housing member comprises a port. The housing members are adapted to be joined together either directly or through one or more intermediate housing assembly elements such as a spacer housing, as described herein. All housing assembly elements are configured to provide a fluid-tight seal when mated. Suitable mating pair members for the various housing assembly components include, but are not limited to threaded connectors, snaps, notches and detents, frictional/slip fittings, and the like.

As used herein, the term "lateral" is relative and refers to the direction towards the ports in the assembled device. Likewise, the term "medial: refers to the direction towards the center of the assembled device.

The one or more cutting elements may be present in any number suitable for the desired purposed (e.g., one, two, three, four, five, six, or more cutting elements may be present) and the cutting elements may be the same or different, as described herein. For example, the cutting elements may include slicers and choppers as described herein. The cutting elements generally are configured to fit and be held firmly within the housing assembly. The cutting elements are generally structured as grids or are grid-like wherein they are defined as having a plurality of rigid members defining apertures. The apertures may be any suitable shape for the desired application and tissue type of interest. For example, apertures may be generally circular, oval, or ovoid, triangular, square, rectangular, diamond-shaped, or any other quadrilateral, or higher order multi-sided shape (e.g., pentagonal, hexagonal, etc.). The cutting elements are arranged perpendicular to the fluid flow path such that the apertures are in-line with the fluid flow path. In other words, fluids flowing from one port to the other port along the fluid flow path pass through the apertures.

As used herein, the term "length" when describing a cutting member aperture is intended to generally refer to the longest dimension of aperture. For example, for circular apertures, "length" refers to the circumference; for triangular apertures, "length" refers to the longest vertex; for square, rectangular, or quadrilateral apertures, "length" refers to the longest diagonal (corner to corner); and the like. In some embodiments, the apertures have a length of 0.1 mm-10.0 mm.

As used herein, the term "grid" when describing a cutting element (e.g., a chopper or slicer) does merely refers to a regular or irregular array of apertures and does not necessarily imply that the apertures are square or rectangular in shape. For example, FIG. 14 illustrates a chopper having apertures arrayed in a "spider grid" pattern.

The cutting element members (e.g., the chopper members and the slicer members) are the internal support members that define the apertures. The cutting element members have at least one cutting edge on the front side, the back side, or both. The cutting edges face the direction of fluid flow such that any aggregates of cells or other particulate matter traveling along the fluid flow path from one port to the other port encounter the cutting edge before flowing through the apertures.

As discussed herein, the device is used to size tissue (e.g., adipose tissue) aspirates prior to implantation. Typically, the tissue is harvested from the donor using a collection (first) syringe according, to standard methods. The harvested tissue is then passed from the collection (first) syringe into a second syringe through the device once (i.e., in one direction) or back-and-forth one, two, three, four, five, six, or more times. In preferred embodiments, the tissue sample is passed from the first syringe to the second syringe and back to the first syringe at least once.

In one aspect, the device comprises only a single cutting element. This cutting element may conform generally to the specifications of a chopper or a slicer as described herein and have aperture lengths of 0.1 mm-10.0 mm. The cutting element members may have a cutting edge on one or both faces. It is preferable that the cutting element members have cutting edges on both faces such that the tissue is effectively deagglomerated when transferred between the syringes in both directions.

In another aspect, the device comprises two cutting elements and optionally contains an O-ring between the cutting elements. The O-ring may be a separate element or be integrated into one or both of the cutting elements. In some embodiments, the two cutting elements are identical. In some embodiments the cutting element members have cutting edges on only one face, wherein the cutting faces are lateral-facing (i.e., the non-cutting faces of the two cutting elements are medial facing and placed "back-to-back"). In other embodiments, both sides of the cutting elements have cutting edges on the cutting element members.

In another aspect, the device comprises three cutting elements and optional contains integrated or separate O-ring(s) between one or more of the cutting, elements. In one embodiment, the first and third cutting elements are laterally-disposed and the second cutting element is medially-disposed (i.e., sandwiched between the first and third cutting elements), wherein the first and third cutting elements have larger apertures than the second cutting element. Optionally, the first and third cutting elements are substantially identical. In some embodiments, the first and third cutting elements having cutting edges only on the lateral-facing surface. In other embodiments, the first and third cutting elements have cutting edges on both the lateral-facing and medial-facing surface and/or optionally conform to the description of a chopper as described herein. In other embodiments, the second cutting element has cutting edges on both faces and/or optionally conform to the description of a slicer as described herein.

In another aspect, the device comprises four cutting elements and optionally contains integrated or separate O-ring(s) between one or more of the cutting elements. In one embodiment, the first and fourth cutting elements are laterally-disposed and the second and third cutting elements are medially-disposed (i.e., sandwiched between the first and fourth cutting elements), wherein the first and fourth cutting elements have larger apertures than the second and third cutting elements. In some embodiments, the first and fourth cutting elements are substantially identical and/or optionally conform to the description of a chopper as described herein. In some embodiments, the second and third cutting elements are substantially identical and/or optionally conform to the description of a slicer as described herein. In some embodiments, the first and fourth cutting elements having cutting edges only on the lateral-facing surfaces. In other embodiments, the first and fourth cutting elements have cutting edges on both the lateral-facing and medial-facing surfaces. In some embodiments, the second and third cutting elements having cutting edges on both the lateral-facing and medial-facing surfaces.

In other aspects, the device comprises two, three, four, five, six, seven, eight or more cutting elements, as described herein. All cutting elements may be identical or may be different. It is generally preferred that the cutting elements are arranged such that the configurations and cutting surfaces are symmetrical whether the device is used in the "forward" or "backward" direction. Furthermore, it is generally preferred that, if all cutting elements are not identical, the aperture size generally decreases in the lateral to medial direction. For example, if an odd number of cutting elements is used, the cutting elements are arranged in a symmetrical pattern such as 1-2-3-2-1, wherein cutting elements 1 have the largest aperture size which progressively decreases to cutting element 3. Likewise, if an even number of cutting elements is used, the cutting elements may be arranged in a symmetrical pattern such as 1-2-3-3-2-1.

In some embodiments of the foregoing aspects, the invention provides a kit comprising two housing members, one or more spacer housings of variable sizes, and a plurality of cutting elements. The housing assembly members are adapted to accept a variable number of cutting elements which may be selected and sequenced by the user. For example, the system may provide housing members which, when mated, hold a single cutting element within the inner volume, and further provide one or more spacer housings in which may be used individually or in series to increase the number of cutting members that can be retained within the housing assembly. Similarly, the plurality of cutting elements may be identical, have varying aperture size, or a combination of both in order to provide the most flexibility to the user in configuring the device.

Other aspects and embodiments of the present invention are understood with reference to the figures and following description.

BRIEF DESCRIPTION OF THE DRAWINGS

FIG. 1 is a perspective view of the tissue deagglomerator device in use and attached to two syringes.

FIG. 2 is disassembled view of the tissue deagglomerator device and the two syringes as illustrated in FIG. 1.

FIG. 3 is an exploded view of one configuration of the tissue deagglomerator device of the present invention.

FIG. 4 is a perspective view of a slicer as may be used in the deagglomeration assembly.

FIG. 5 is a schematic cross-sectional view of the unassembled device shown in FIG. 3.

FIG. 6 is a schematic cross-sectional view of the assembled device shown in FIG. 3.

FIG. 7 is a schematic cross-sectional view of a slicer, as illustrated in FIG. 6.

FIG. 8 is a perspective view of another configuration of an assembled tissue deagglomerator device that includes a spacer housing.

FIG. 9 is an exploded view of the tissue deagglomerator device illustrated in FIG. 8.

FIG. 10 is a schematic cross-sectional view of the assembled device shown in FIG. 8.

FIG. 11 is a perspective view of another configuration of an assembled tissue deagglomerator device having an alternate housing member design.

FIG. 12 is an exploded view of the tissue deaggloinerator device illustrated, in FIG. 11.

DETAILED DESCRIPTION OF THE DISCLOSURE

Figure 15:
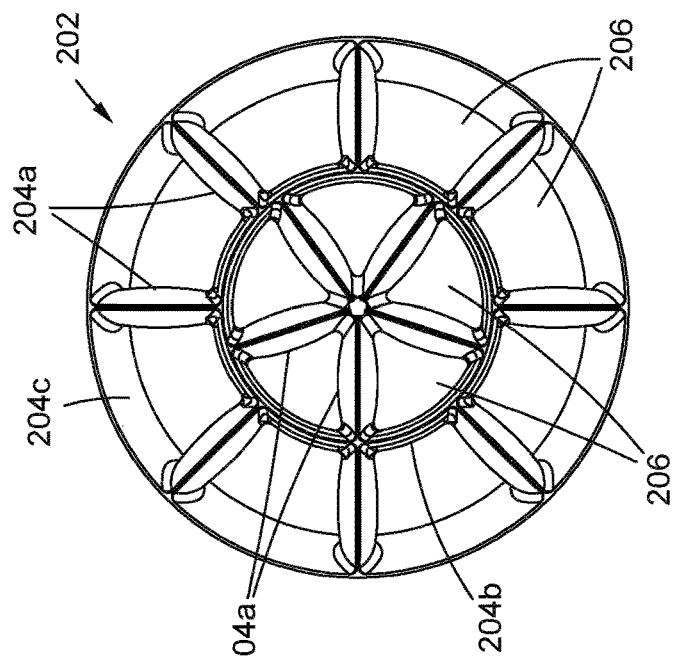
FIG. 15 is a schematic plan view of a back side of a chopper.

The invention provides a tissue homogenizer that is adapted to deagglomerate tissue samples by breaking down relatively large cell clusters into smaller clusters and/or individual cells without significantly damaging the cells. The inventive devices have particular utility for processing adipose tissue for homologous transplantation in cosmetic procedures. In these procedures, it is common for the adipose tissue to be removed from one area of the patient (e.g., the subcutaneous hip area or abdomen) and injected into another area (e.g., the lips, facial wrinkles, etc.) for cosmetic benefit and wherein improved outcomes may be achieved by injecting/transplanting a smoother tissue product having smaller cell clusters and agglomerations. However, upon initial removal from the patient's body, the adipose tissue may include agglomerated clumps of fat cells that may too large to be reinjected into the patient and/or reinjection of those agglomerations may not result in the desired cosmetic effect. For example, the extracted masses of fat cells may be too large to pass through minimally invasive thin needles that may be required for certain medical procedures, or the large masses may result in a lumpy appearance when injected subcutaneously. Additionally, smaller-sized cell aggregates may allow better interaction of stem cells and other cells with those present at the injection site. Accordingly, deagglomeration of cell clusters prior to implantation may improve both the cosmetic and therapeutic efficacy of the procedure.

The deagglomeration procedure preferably does little or no damage to the intact cells themselves but instead merely breaks the larger cell clusters into smaller ones or even to single cells. Deagglomeration is preferable to the filtering techniques of the prior art because filtering is based on the simple removal of larger cell clusters (e.g., by size exclusion) and necessarily reduces the yield of viable cells from the extraction procedure. Deagglomeration, on the other hand, retains more of the viable extracted cells.

FIG. 1 illustrates the manner of using device 10 which is helpful in understanding the components and relationship among the components. Device 10 is configured to provide a fluid flow path between two syringes 1,2. Tissue 12 from the patient collected in the first syringe 1 is passed through device 10 and into the second syringe 2. As the tissue passes through device 10 in forward direction A1, large cell agglomerates are deagglomerated into smaller masses of cells. The tissue may then be passed from the second syringe 2 through device 10 in the reverse direction A2, back into the first syringe 1 in order to provide further deagglomeration. In this way, the device may be bidirectional. This bidirectional processing may continue for 1, 2, 3, 4, 5, 6, 7, 8, 9, 10 or more cycles and/or until the overall tissue sample may be deagglomerated into masses of the desired size. The final tissue preparation 14 may reside either in the first syringe 1, second syringe 2, or may be split between the first syringe 1 and the second syringe 2, as desired by the user.

FIG. 2 shows an exploded view of the assembled device 10 in relation to the syringes 1,2. Device 10 provides a substantially leak-free fluid flow path between the syringes 1,2 in order to form a closed system so as to prevent contact between the tissue and the outside environment and to prevent loss of tissue during processing. This may ensure that the tissue may not be contaminated or otherwise compromised during the procedure. Syringes 1,2 may be standard medical syringes characterized by a plunger 1a, 2a for generating positive and negative pressures within the syringe barrel for dispensing and drawing fluids, respectively. Syringes 12 also have tips 1b, 2b capable of forming a fluid-tight seal with device 10. In some embodiments, tips 1b,2b on syringes 1,2 and ports 11a,b on device 10 are standard Luer lock connectors. In use, it is preferred that device 10 is configured such that the tissue sample may be pushed between syringes 1,2 solely by applying positive pressure to the syringe plunger initially containing the tissue sample. However, for samples that are viscous and/or have particularly large cell agglomeration, it may be necessary to simultaneously apply a negative pressure using plugger of the receiving syringe.

Generally, device 10 comprises a housing assembly 100 which makes up the outer body and an internal deagglomeration assembly 200 which optionally comprises various elements that together are adapted to deagglomerate tissue samples. The deagglomeration assembly optionally included elements including, for example, one or more choppers 202, slicers 222, and O-rings 122. The deagglomeration assembly 200 including its various subcomponents is housed within housing assembly 100.

As used herein, chopper 202 is a deagglomeration assembly 200 element that has chopper members 204 defining chopper apertures 206 and wherein at least one face (or both faces) of chopper 202 have chopper members 204 with a forward-facing cutting edge rather than rounded or squared edges as is typical of a standard wire or plastic mesh. Chopper apertures 206 have a longest dimension of about 0.5-10 mm but in any event are longer/larger than slicer apertures 226.

As used herein, slicer 222 is a deagglomeration assembly 200 element that has slicer members 224 defining slicer apertures 226 and wherein at least one face (or both faces) of slicer 222 have slicer members 224 with a forward-facing cutting edge rather than rounded or squared edges as is typical of a standard wire or plastic mesh. Slicer apertures 226 have a longest dimension of about 0.2-2.5 mm but in any event are shorter/smaller than chopper apertures 206.

O-rings 122 are used as spacers between adjacent chopper 202 and/or slicer 222 because it may be desirable to have a fluid space between the cutting elements. Additionally, O-rings 122 may be placed between the inner surface of housing assembly 100 elements and the outermost cutting element (chopper 202 or slicer 222) in order to stability all deagglomeration assembly 200 elements within the assembled housing assembly 100.

Each of the elements is described in detail below with reference to FIGS. 3-17.

The Housing Assembly

The outer body of device 10 comprises housing assembly 100 that encloses and houses deagglomeration assembly 200. Housing assembly 100 may include a variety of elements as described below.

In one embodiment, housing assembly 100 comprises two housing members 102a,b that form an inner volume when mated and are adapted to house deagglomerating assembly 200 within the inner volume. Housing members 102 may have any convenient shape but a circular cross-section (looking into the housing member interior opening 108). However, housing members 102 and the housing member opening 108 also may include cross-sections of other shapes such as octagonal, oval shaped, square, other shapes and any combinations thereof. In preferred embodiments, housing member 102 may be generally frustoconical in shape terminating the port 11 at its apex.

As illustrated in the various figures, a frustoconical shape is usually preferred for housing members 102a,b, wherein the cylindrical portion of the housing members 102a,b are adapted to be mated and form a fluid-tight seal. The conical portion of housing member 102 provides a small void volume and transitions the fluid flow path from the narrow diameter of port 11 to the larger diameter of the cylindrical portion which forms the body of device 10. Each of housing members 102a,b further comprises a port 11 which is adapted to connect to tip 22 of syringe 20. Preferably, port 11 is a standard Luer lock mating pair member which, in combination with the complimentary Luer lock mating pair member on a standard syringe, forms a fluid-tight seal when mated. In other embodiments, port 11 comprises Luer-Slip fittings. It is understood that the scope of the device 10 is not limited in any way by the specific configuration of port 11 and/or how it is connected to tips 1b,2b of syringe 1,2. Port 11 also may include tubing or other types of passageways that extend from housing member 102 to the syringe tip 1b in order to provide a fluid flow path.

As noted above, housing members 102a,b are generally symmetrical but are adapted to be mated and form a fluid-tight seal. The mating mechanism may be reversible or irreversible depending upon the specific need and intended use. Most conveniently, housing members 102a,b are manufactured and/or provided as separate elements in order to permit loading and configuration of deagglomeration assembly 200 but wherein device 10 cannot be disassembled/reassembled once housing members 102a,b are mated. In one embodiment illustrated in FIG. 3, housing members 102a,b are mated using complimentary threaded connectors 105a,b such that housing members 102a,b may be screwed together. In another embodiment illustrated in FIGS. 5-6, housing members 102a,b are mated using a notch and detent system 104. Alternatively, housing members 102a,b may be mated using a simple friction fit in which the body of one housing member 102a is designed to slide securely into the opening 108 of the other housing member 102b.

Housing assembly 100 optionally may include spacer housing 128 as illustrated in FIGS. 9-10. Spacer housing 128 is adapted to extend the length of housing assembly 100 in order to provide more internal volume for larger deagglomeration assemblies 200. Spacer housing 128 may be provided in a variety of lengths in order to provide a modular device 10 system. As discussed in more detail below, a device 10 system may be designed such that housing members 102a,b alone accept a single deagglomeration assembly 200 element (e.g., a chopper 202 or a slicer 222). One or more spacer housings 128 of different lengths may be provided and sized such that the length of the fully assembled housing assembly 100 (including housing members 102a,b and spacer housing 128) accept additional deagglomeration assembly 200 elements. FIG. 9 illustrates spacer housing 128 having threaded connectors 105a,b, and FIG. 10 illustrates spacer housing 128 having a notch and detent system 104. It is understood that the specific connection mechanism is not limiting or limited to those illustrated here.

In another embodiment shown in FIGS. 3 & 5, housing member 102 optionally includes one or more cutting blades 112 (e.g., 1, 2, 3, 4, 5, 6, 7, or more) that may be positioned on the inner surface of housing member 102 and within the housing member interior opening 108. In one embodiment, the cutting blades 112 generally extend longitudinally and/or at any angle of orientation from the port 11. Cutting blades 112 have at least one sharp edge and are adapted and designed to break down the largest tissue agglomerates which may reduce clogging of the finer deagglomeration elements such as chopper 202 and slicer 222. Optional cutting blades 112 may be present on either one of housing members 102a or 102b, or both.

In some embodiments, the entire lengths of the cutting blades 112 may be affixed to the inner surface of housing member 102 (e.g., see cutting blade 112a in FIG. 5). In other exemplary embodiments a first end of a cutting blade 112 may be affixed to an inner surface of housing member 102 and a second end of the cutting blade 112 may extend freely into the interior volume and away from the surface (e.g., see cutting blade 112b in FIG. 5). The cutting blades 112 may be attached to an inner surface 110 using adhesive, welding, pressure fit into receiving holes, channels, other types of attachment mechanisms or methods and any combination thereof. Alternatively, cutting blades 112 and housing member 102 may be co-molded or otherwise formed together integrally.

In another embodiment, housing member 102 may include support posts 124 that may extend from inner surface of housing member 102 to an inserted deagglomerating assembly 200 element. Posts 124 may thereby provide lateral support to the deagglomeration assembly 200. It may be preferable that the support posts 124 abut the front and/or the back of a chopper 202 and/or a slicer 222 (depending on the configuration as described in other sections) to provide support from both sides directly to the chopper 202 and/or the slicer 222 itself. This may help secure and hold the deagglomeration assembly 200 in place during use of the device 10. Any number of support posts 124 may be used on either side of the deagglomeration assembly 200 as required.

The housing member 102 may be about 1-5 centimeters in diameter (e.g., about 1, 2, 3, 4, or 5 cm), but other diameters may be used. Housing assembly 100, like all components of device 10, may be formed from of any suitable material including, for example, polystyrene, polypropylene, polyethylene, or other types of suitable materials Deagglomeration Assembly Device 10 includes a deagglomeration assembly 200 enclosed in housing assembly 100. Deagglomeration assembly 200 includes one or more elements described below which may be present individually or in any combination.

Deagglomeration Assembly—Chopper 202

Figure 13:
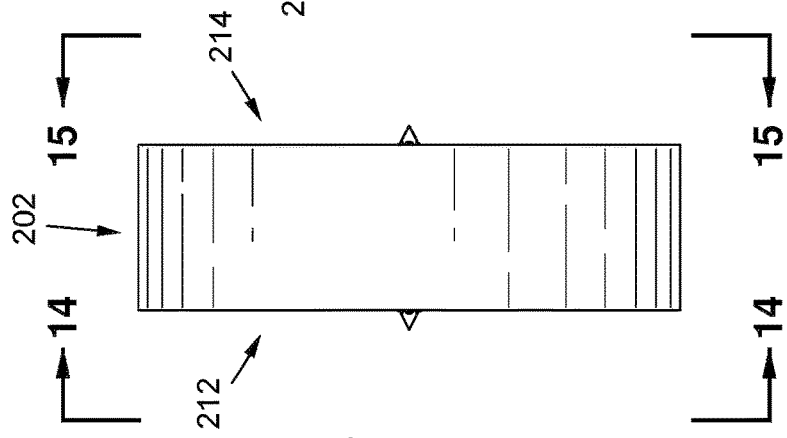
FIG. 13 is a perspective side-view of a chopper.
Figure 14:
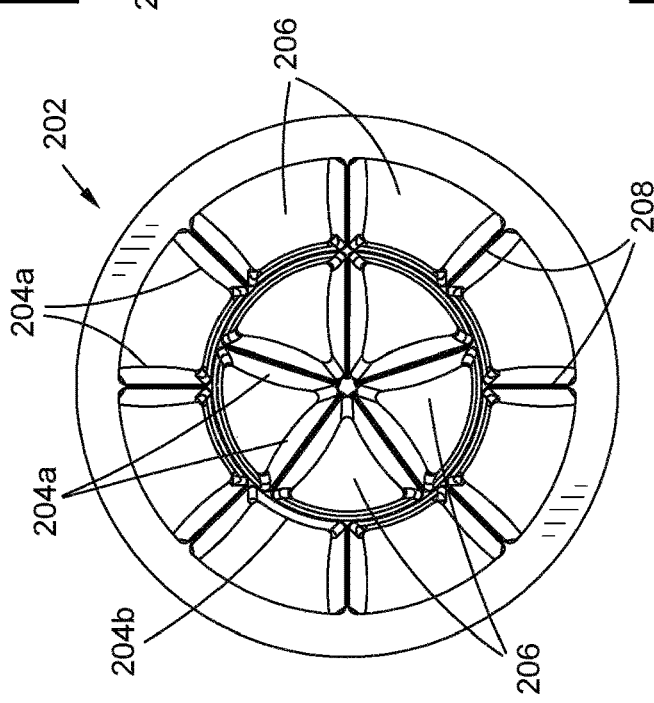
FIG. 14 is a schematic plan view of a front side of a chopper.

In some embodiments, the deagglomeration assembly 200 includes one or more choppers 202. As shown in FIGS. 13-15, chopper 202 is has the same general cross-sectional shape as, and is adapted to fit snugly within housing assembly. In one embodiment, chopper 202 is a disk-shaped grid of chopping members 204 that may be arranged to define a plurality of chopping apertures 206. In one embodiment, the chopping members 204 may be arranged as concentric ring members 204b with interspaced radial members 204a (e.g., spokes) extending between the rings. Chopper 202 may include two concentric ring members 204b with the outermost ring 204c defining the outer rim of the chopper 202. Other numbers of rings (e.g., one, two, three or more concentric ring members) may be used. Radial members 204a may or may not be contiguous through the concentric ring members(s) 204b. This formation of concentric rings and radial spokes may also be referred to as a spider grid. Chopping apertures 206 are defined by the concentric rings 204b and the radial members 204a.

In another embodiment, chopping members 204 may be arranged in a grid-like formation of rows and columns that form corresponding rows and columns of chopping apertures 206. Chopping members 204 may be approximately linear sections such that four chopping members 204 may form a generally square-, rectangular-, diamond-, or other quadrilateral-shaped chopping aperture 206 (with each chopping member 204 forming a side wall of chopping aperture 206).

In some embodiments, the dimensions of chopping apertures 206 are designed to break the larger clusters of cells into smaller or medium-sized clusters that may then be broken down into even smaller desired sizes by additional elements (e.g., slicing grids 216) as will be described in other sections. Accordingly, the area of chopping apertures 206 is less than that of slicing apertures 226. In some embodiments, the dimensions of the chopping apertures 206 are about 0.5-10 mm in the longest dimension including, for example at least 0.5, 1.0, 2.0, 3.0, 4.0, 5.0, 6.0, 7.0, 8.0, 9.0, or 10.0 mm or not more than 0.5, 1.0, 2.0, 3.0, 4.0, 5.0, 6.0, 7.0, 8.0, 9.0, or 10.0 mm.

Choppers 202 are shaped to fit snugly within the inner volume of housing members 102. It is understood that choppers 202 therefore have the same cross-sectional shape as housing members 102 and are sized to provide a frictional fit with the inner surface 110 of housing member 102 such that substantially all of the tissue sample flows though chopping apertures 206 during normal use, rather than between the outer surface of chopper 202 and inner surface 110.

Chopper 202 may be defined as having a front face 212 and a rear face 214. Front face 212 is characterized in that chopping members 204 comprise a cutting edge 208. Rear face 214 may be characterized in that chopping members 204 have a cutting edge 208 or are is substantially flat (i.e., lacking cutting edge 208). Chopping members 204 that have cutting edge 208 may be used when additional cutting surfaces are desired for deagglomeration of tissue samples and/or if deagglomeration assembly 200 comprises only a single chopper 202 and/or the single chopper 202 is the only deagglomeration element in the deagglomeration assembly 200. Chopping members 204 that are substantially flat may aid in providing a more compact design and cause less damage to the harvested cells during the deagglomeration process.

Cutting edges 208 may be sharp along the length (preferably along its entire length) and may result from the shape formed of chopping members 204. For example, chopping members 204 may have any convenient shape that presents an acute angle at front face 212 such as triangle or other wedge. Cutting edges 208 are adapted to slice or otherwise break up the agglomerated fat clusters that may be impressed upon the front face 212 as the fat tissue may be forced through the chopper 202 from its front face 212 to its back face 214. It also is preferable that the sharpness of cutting edges 208 be not too sharp so that they may not damage the fat cells that may come into contact with them. It also is preferable the edges 208 not be coarse so that they may not snag or otherwise prevent the adipose clusters from passing through the apertures 206. In this way, clusters of adipose cells that may be larger in size than the chopping apertures 206 may be forced through the apertures 206 from the front 212 and broken down by the slicing action of the chopping members 204 and their corresponding sharp front edges 208. The edges 208 may be sharpened as a result of the molding process or may be sharpened during a secondary sharpening procedure as required. In addition, the edges 208 may be re-sharpened at any time as necessary.

Deagglomeration Assembly—Slicer 222

The deagglomerating assembly 200 also may include one or more slicers 222. As shown in FIG. 4, slicer 222 may comprise a plurality of slicer members 224 that may be arranged to define a plurality of corresponding slicer apertures 226. The slicer 222 may be a disk-shaped or may include other shapes. Slicer 222 design considerations are similar to those for chopper 202 except that the slicer apertures 226 are smaller than chopper apertures 206 and slicer members 224 have the same or smaller dimensions/thickness compared to chopper members 204. It is generally intended that slicer 222 produces smaller cell clusters than chopper 202. Optionally, slicer 222 comprises an integrated O-ring 122 on the front/lateral side, the back/medial side, or both. O-ring 122 may be used for spacing to a secure deagglomeration assembly 200 elements snugly within housing assembly 100.

In some embodiments, the dimensions of slicing apertures 226 are designed to break the smaller or medium-sized clusters of cells into even smaller clusters and/or even individual cells. Accordingly, the area of slicing apertures 226 is greater than that of chopping apertures 206. In some embodiments, the dimensions of the chopping apertures 206 are about 0.05-2.5 min in the longest dimension including, for example at least 0.05, 0.1, 0.2, 0.3, 0.4, 0.5, 0.6, 0.7, 0.8, 0.9, 1.0, 1.2, 1.4, 1.6, 1.8, 2.0, 2.25, or 2.50 mm or not more than 0.1, 0.2, 0.3, 0.4, 0.5.0.6, 0.7, 0.8, 0.9, 1.0, 1.2, 1.4, 1.6.1.8, 2.0, 2.25, or 2.50 mm.

Slicers 222 are shaped to fit snugly within the inner volume of housing members 102. It is understood that slicers 222 therefore have the same cross-sectional shape as housing members 102 and are sized to provide a frictional fit with the inner surface of housing member 102 such that substantially all of the tissue sample flows though slicer apertures 226 during nominal use, rather than between the outer surface of slicer 222 and inner surface of housing member 102.

In one embodiment illustrated in FIG. 4, the slicer members 224 are arranged in a grid-like or matrix formation of rows and columns that may form corresponding rows and columns of slicer apertures 226. In this example, each slicer member 224 may be a generally straight section such that four slicer members 224 may form a generally square-, diamond-, or other quadrilateral-shaped slicer aperture 226 (with each slicer member 224 forming a side wall of the slicer aperture 226).

As illustrated in FIG. 7, slicer 222 may be defined as having a front face 232 and a rear face 234. Front face 232 is characterized in that slicing members 224 comprise a cutting edge 228. Rear face 234 may be characterized in that slicing members 224 have a cutting edge 228 or are is substantially flat (i.e., lacking cutting edge 228). Slicing members 224 that have cutting edge 228 may be used when additional cutting surfaces, are desired for deagglomeration of tissue samples and/or if deagglomeration assembly 200 comprises only a single slicer 222 and/or the single slicer 222 is the only deagglomeration element in the deagglomeration assembly 200 Slicing members 224 that are substantially flat may aid in providing a more compact design and cause less damage to the harvested cells during the deagglomeration process.

Cutting edges 228 may be sharp along the length (preferably along its entire length) and may result from the shape formed shape of slicing members 224. For example, slicing members 224 may have any convenient shape that presents an acute angle at front face 232 such as triangle or other wedge. Cutting edges 228 are adapted to slice or otherwise break up the agglomerated fat clusters that may be impressed upon the front face 232 as the fat tissue may be forced through the slicer 222 from its front face 232 to its back face 234. It also is preferable that the sharpness of cutting edges 228 be not too sharp so that they may not damage the fat cells that may come into contact with them. It also is preferable the edges 228 not be coarse so that they may not snag or otherwise prevent the adipose clusters from passing through the apertures 226. In this way, clusters of adipose cells that may be larger in size than the slicing apertures 226 may be forced through the apertures 226 from the front 232 and broken down by the slicing action of the slicing members 224 and their corresponding sharp front edges 228. The edges 228 may be sharpened as a result of the molding process or may be sharpened during a secondary sharpening procedure as required. In addition, the edges 228 may be re-sharpened at any time as necessary.

In one embodiment, the dimensions of the slicing apertures 226 may be chosen to generally correspond to the maximum desired size of the re-sized adipose cell clusters that may pass through slicer 222 (either from the front 232 or from the back 234). In this way, as the masses of agglomerated adipose cells may pass through the slicer apertures 226, the tissue masses may be generally resized to the size of the slicer apertures 226. Note that the dimensions of the slicer apertures 226 may be smaller than the dimensions of the chopping apertures 206. For example, in one embodiment it may be preferable that the slicer apertures 226 each have a width of about 50 µm (this may be approximately the size of nano-fat particles). In another embodiment it may be preferable that the slicer apertures 226 each have a width of about 100 µm. In addition, depending on the medical procedure that may ultimately utilize the resized adipose cell masses, it may be preferable that the slicing apertures 226 each have a width of about 50 µm-2000 µm or 100 µm-1500 µm. Other widths may also be used depending on the ultimate purpose of the resized tissue masses, and the scope of the device 10 is not limited in any way by the widths of the slicer apertures 220.

Figure 18:
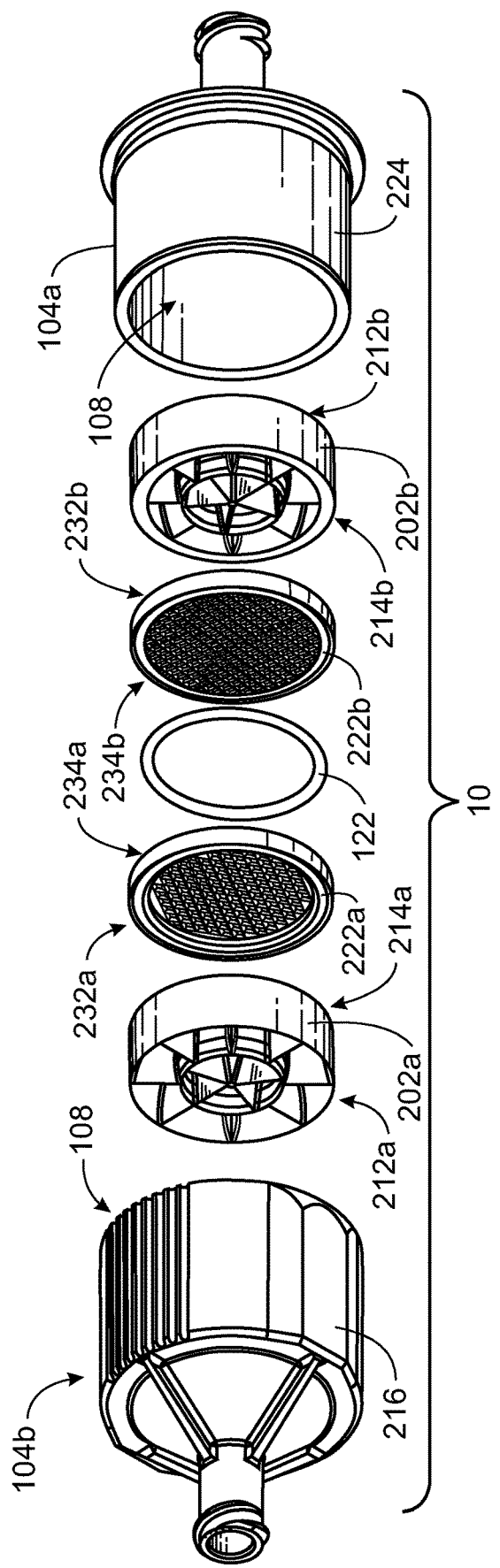
FIG. 18 is a perspective view of another configuration of an assembled tissue deagglomerator device having an alternate housing member design.

When a plurality (2, 3, 4, or more) slicers 222 are present, slicing apertures 226*a* of the first slicer 222*a* need not match or align with the slicing apertures 226*b* of the second slicer 222*b* (or any subsequent slicer 222) in size, shape, or orientation. For example, in FIG. 18, the second slicer 222*b* is oriented at an acute angle with respect to the first slicer 222*a*. In fact, having different sized and shaped slicing apertures 226 on the slicers 222 may allow for the formation of a smaller functional aperture than any individual aperture 226. For example, in FIG. 18, the slicing apertures of the second slicer 222*b* are smaller than the slicing apertures of the first slicer 222*a*.

In one configuration, the slicing members 224 and the slicing apertures 226 of the first and second slicers 222*a,b* respectively may be generally aligned. In another configuration, the second slicer 222*b* is rotated about its center axis by, for example, 90° with respect to the first slicer 222*a*. This may place the apex or junction of four slicing members 224 in one slicer 222*b* in the center of the slicing apertures 226*a* in the other slicer 222*a*. That is, looking through the slicing apertures 226*a* of slicer 222*a*, one may see a "+" (cross) formation created by the junction of the slicing members 224*b*. It is understood that while this example depicts one of the slicers 222 offset by 90°, either of the slicers 222 may be offset by other angles or orientations to create other sized combined apertures 226. Note also that if the slicing apertures 226 may be of other shapes (e.g., circular), the rotational offset of one or more of the slicers 222 may result in the formation of other sized and/or shaped combined apertures 226.

Device Assemblies

In some embodiments, the device 10 may include a deagglomerating assembly 200 enclosed within a housing assembly 100. In various embodiments, the deagglomeration assembly 200 includes a combination of some or all of the elements described above.

FIGS. 3 and 5-6 illustrate one embodiment of device 10 according to the present invention. FIG. 3. shows an exploded view of device 10 which has a first housing member 102a, a second housing member 102, a slicer 222, and two laterally-disposed O-rings 122. Housing members 102a,b are frustoconical in shape terminating with Luer connectors at tips 1a,1b at the apex. Housing members 102a,b are illustrated in FIG. 3 as being engaged via threaded connectors 105a,b but it is understood that these elements may be substituted with any appropriate connector system or pair members that create a fluid-tight seal and hold deagglomeration assembly securely inside. For example, a notch and detent system is illustrated in FIGS. 5-6. Housing members 102a,b are further illustrated as having cutting blades 112. It is understood that cutting blades 112 are optional and may be omitted. This embodiment illustrates a deagglomeration assembly 200 having a single cutting element, slicer 222. It is understood that chopper 202 may be substituted for slicer 222. It is preferred that, for a deagglomeration assembly 200 having a single cutting element, that cutting element with have cutting edges on both faces so that the device is adapted to deagglomerate the tissue sample as the tissue is pushed in both the forward and reverse directions. This embodiment illustrates the presence of two O-rings 122 and multiple support posts 124 that are used to secure slicer 222 within housing assembly 100. It is understood that one or both of O-rings 122 may be integrated with slicer 222 as a rim in order to achieve the same purpose. Support posts 124 also are optional.

FIGS. 5-6 illustrate one embodiment that may be used to secure a single cutting element deagglomeration assembly 200. In this case, the cutting element is shown as slicer 222. Housing members 102a,b are mated as described herein to form the housing assembly 100, and in doing so, a circumferential notch 120 (or channel) may be formed. Notch 120 has a width that corresponds to the width of the slicer 222 such that slicer 222 is received into the notch 120 and held securely therein either alone or in conjunction with support posts 124 and/or O-rings 122. In this way, the slicer 222 may be snugly secured within the mated housing members 102a,b to form the device 10. 100861 FIGS. 8-10 illustrate another configuration of device 10. In this embodiment, housing assembly 100 comprises a first and second housing member 102a,b and spacer housing 128 which is sized to allow for the incorporation of a second cutting element as part of deagglomeration assembly 200. FIG. 8 shows a perspective view of assembled device 10 including first and second housing member 102a,b and spacer housing 128. FIG. 9 illustrates that the elements of housing assembly 100 may be engaged via threaded connectors 105a,b, but it is understood that other connector systems may be used including, for example, an notch and detent system 104 as illustrated in FIG. 10. FIG. 9 further illustrates another configuration of deagglomeration assembly 200 which includes two slicers 222a,b and three O-rings 122a,b,c. FIG. 10 illustrates that the introduction of spacer housing 128 creates notch 120 which is larger than notch 120 in FIG. 6, and begin adapted to accept and secure a larger deagglomeration assembly 200. Although this embodiment is illustrated with spacer housing 128 adapted to accept two cutting elements (slicers 222a,b), it is understood that spacer housing 128 may be modified to accept 3, 4, 5, 6, or more cutting elements that may be a mixture of slicers 222 and choppers 202.

FIGS. 11, 12, 16, and 17 illustrate another configuration of device 10. FIG. 11 shows a fully assembled device of this embodiment including housing assembly 100 comprises a first and second housing member 102a,b which are large enough to accommodate a deagglomeration assembly 200 having multiple (four, in this case) cutting elements. As shown in FIG. 12, housing members 102a,b are engaged using a notch and detent 104a,b system. In some embodiments, this system forms an irreversible engagement. In this embodiment, deagglomeration assembly 200 contains a first and second chopper 202a,b and a first and second slicer 222a,b. Choppers 202a,b are disposed laterally relative to slicers 222a,b. In one configuration, choppers 202a,b have cutting edges 208 on the front face 212a,b which are lateral facing and have flat and/or non-cutting edges on medial-facing rear face 214a,b. In one configuration illustrated here, slicers 222a,b have cutting edges 228 on front faces 232a,b and rear faces 234a,b. Optionally, O-ring 122 is disposed between the first slicer 222a and the second slicer 222b in order to promote more efficient tissue deagglomeration. As discussed above, O-ring 122 may be integral to either or both of slicers 222a,b. Optionally, although not illustrated, O-rings 122 may be placed between each chopper 202 and slicer 222.

Figure 16:
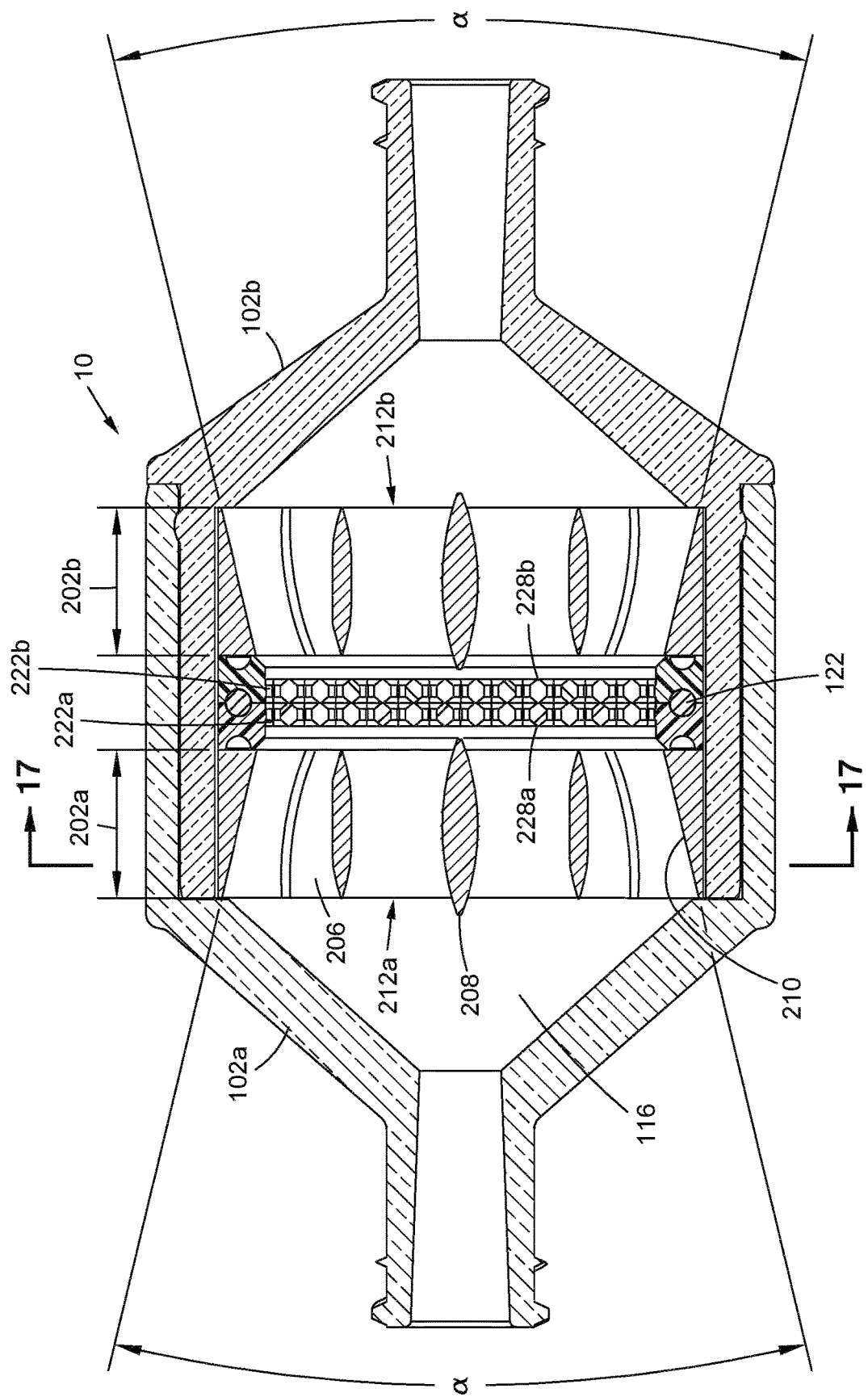
FIG. 16 is a cross-sectional plan view of the device shown in FIGS. 11-12.

FIG. 16 shows a cross section of this embodiment in the fully-assembled configuration. Optionally, choppers 202a,b have taper 210 extending in the lateral-to-medial direction. Taper 210 tends to increase the velocity of the tissue sample as it passes through chopper 202 so that it is more effectively deagglomerated by slicer 222. Taper angle α may be about 10°-70° including, for example, about 10°, 20°, 30°, 40°, 50°, 60°, and 70°.

Figure 17:
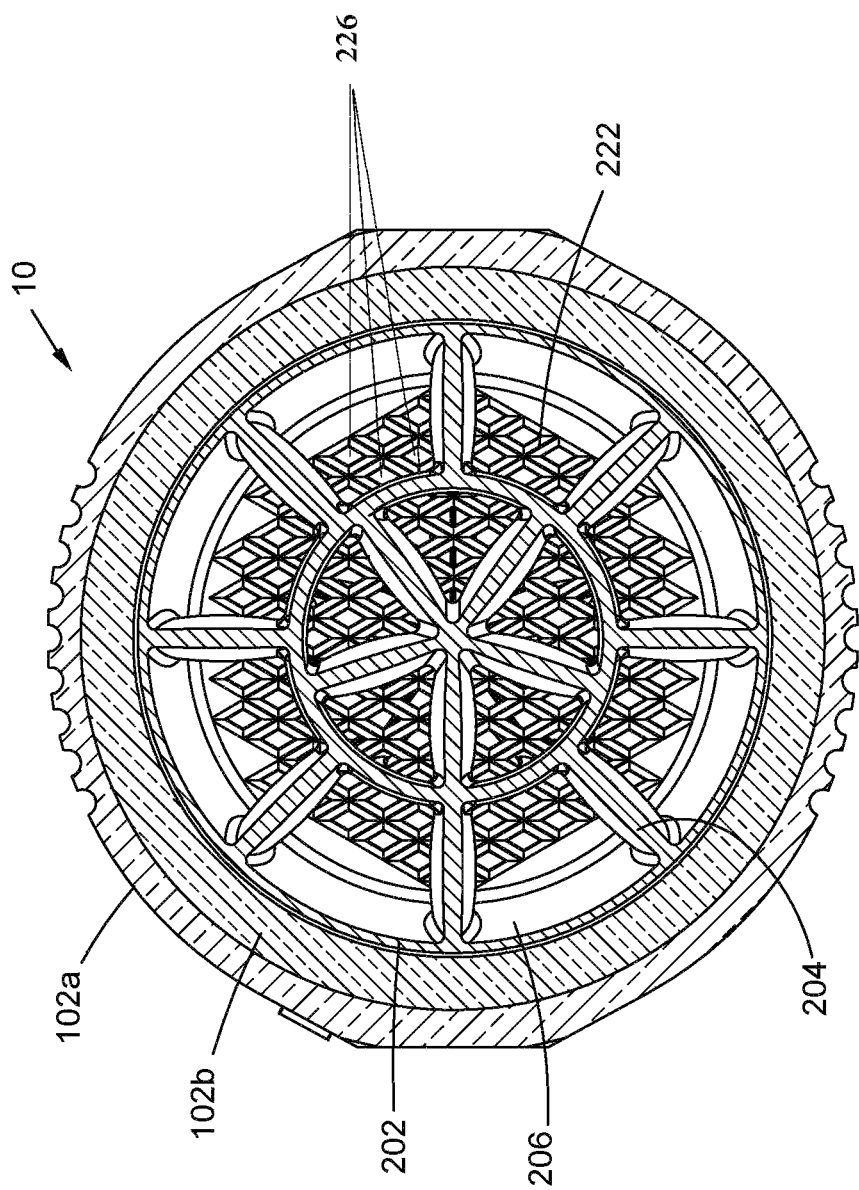
FIG. 17 is a cross-sectional plan view of the device shown in FIGS. 11-12.

FIG. 17 shows a cross-section view down the fluid flow path of device 10 looking from one port 11a in the direction of the other port 11b. This figure illustrates that the tissue sample first encounters chopper 204 with its relatively large apertures 206, and subsequently encounters slicer 222 with its relatively small apertures 226.

The series combination of the elements 202a, 222a, 222b, 202b may preferably fit securely within the inner volume 116 of the housing assembly 100 without gaps or openings between the circumferential surfaces of the elements 202a, 222a, 222b, 202b and the inner surfaces of the housing members 102a,b. This may ensure that tissue passing from the first port 11a to the second port 11b and from second port 11b to the first port 11a must pass through the apertures 206a, 226a, 226b, 206b.

In addition, the series combination of the elements 202a, 222a, 222b, 202b may preferably be held secure from lateral movement within the inner volume 116, especially when force may be applied to the elements 202a, 222a, 222b, 202b by the tissue being pushed through the elements 202a, 222a, 222b, 202b in either direction. The elements 202a, 222a, 222b, 202b may be secured by fitting the elements into circumferential notches or between detents in the inner surfaces by pressure fit, using adhesive, welding or by other attachment methods.

Methods for Use

Device 10 may be used to break down larger sized masses of tissue into smaller sized masses, and the resulting smaller sized masses of tissue may be used for a variety of different medical procedures.

Adipose tissue may be removed from the patient by any adequate procedure (e.g., liposuction) and may be provided into a first syringe 1. With the first syringe 1 containing the adipose tissue, the plunger 1a of the syringe 1 may be fully or partially extended. Device 10 then may be connected to the tip 1b of the first syringe 1 via port 11a. Next, the tip 2b of a second syringe 2 (preferably empty) may be connected to the other port 11b of the device 10. It may be preferable that the plunger 2b of the second syringe 2 be fully inserted. In this way, a leak-proof seal may be formed between the first syringe 1, the device 10 and the second syringe 2.

Next, the plunger 1a of the first syringe 1 may be pressed inward to push the tissue out of the tip 1b of the syringe 1 and into the device 10. As the plunger 1a continues to move inward, the tissue may be forced through the deagglomeration assembly 200 in the direction of arrow A1 thereby being deagglomerated by the choppers 202a,b, the slicers 222a,b, and the cutting blades 112 (depending on the configuration and the elements of the deagglomerating assembly 200 being used).

At the same time, the plunger 2a of the second syringe 2 may be withdrawn to create a negative pressure thereby pulling the tissue from the device 10 and into the second syringe 2. This process may preferably continue until the plunger 1aa may be pressed fully into the syringe 1 (so that all or at least most of the tissue may be pushed out of the syringe 1) and the plunger 2a may be fully extended out from the syringe 2 (so that all or at least most of the tissue may be pulled into the syringe 2).

Next, the plunger 2a of the second syringe 2 may be pressed inward to push the tissue out of the tip 2b of the syringe 2 and into the device 10. As the plunger 2b continues to move inward, the tissue may be forced through the deagglomeration assembly 200 in the direction of A2 thereby being deagglomerated by the choppers 202a,b, the slicers 222a,b, and the cutting blades 112 (depending on the configuration and the elements of the deagglomerating assembly 200 being used).

At the same time, the plunger 1a of the first syringe 1 may be extracted out of the first syringe 1 to pull the tissue from the device 10 and into the first syringe 1. This process may preferably continue until the plunger 2a is pressed fully into the syringe 2 (so that all or at least most of the tissue may be pushed out of the syringe 2) and the plunger 1a may be fully extended out from the syringe 1 (so that all or at least most of the tissue may be pulled into the syringe 1).

This back-and-forth procedure may be repeated as many times as necessary to successfully resize the adipose cell masses to the desired sizes. Once the tissue has been satisfactorily refined to the proper sizes, the tissue may be collected into the first syringe 1, the second syringe 2, or any combination thereof and the device 10 may be removed from the syringes 1,2. The tissue may then be implanted into the patient as required by the medical procedure.

Benefits of the Device

The benefits of the device 10 are multifold, and may include, without limitation, the following benefits:

First, as described in other sections, the device 10 may properly prepare and refine adipose tissue to be of the proper size to be used for certain medical procedures.

Second, the deagglomerating assembly 200 of the device 10 may deagglomerate the adipose masses without unnecessarily damaging the individual fat cells.

Third, the deagglomerating assembly 200 of the device 10 may not filter out the larger adipose masses, but instead may break them down to the desired sizes.

Fourth, the bi-directional functionality of the device 10 may allow for the tissue to be run through the deagglomerating assembly 200 multiple times to ensure that the tissue masses are properly deagglomerated. For example, because the adipose cell masses may be somewhat flexible and amiable, and depending on their orientation, some of the masses may squeeze through the apertures 206, 226 during the first pass (in the direction of arrow A1) through the device 10 without being fully deagglomerated. Accordingly, by enabling multiple passes back-and-forth through the device 10, the device 10 may better ensure that the tissue masses may ultimately be oriented properly while passing through the apertures 206, 226 to be deagglomerated, by the device 10.

Fifth, because it may be impossible to force all of the tissue from the first syringe 1 through the device 10 on the first pass (in the direction of arrow A1) due to the fact that some tissue may remain in the tip 1b and/or in the left housing member 102a of the device 10 when the plunger 1a may be fully inserted into the first syringe 1 and the plunger 2a may be fully extracted from the second syringe 2, some tissue may not be deagglomerated during the first pass through the device 10. Accordingly, upon the second pass through the device 10 (in the direction of arrow A2), the tissue that may not have been deagglomerated in the first pass may be repositioned (being somewhat fluid) within the syringes 1,2 and/or the device 10 so that it may be forced through the deagglomerating assembly 200 during the second pass, or possibly during ensuing passes. In this way, by enabling multiple passes through the device 10, the device 10 may better ensure that all or at least a high percentage of the tissue will ultimately pass through the deagglomerating assembly 200 to be properly deagglomerated.

Sixth, the device 10 may provide a closed system so that the tissue being refined may not come into contact with the outside environment, thus minimizing the chances of contamination.

Those of ordinary skill in the art will appreciate and understand, upon reading this description, that embodiments hereof may provide different and/or other advantages, and that not all embodiments or implementations need have all advantages.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

It is understood by a person of ordinary skill in the art, upon reading this specification, that any of the aspects, elements and/or details of any of the embodiments described herein or otherwise may be combined in any way, and that the scope of the invention includes any combinations of any aspects, elements or details of any of the embodiments hereof.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

What is claimed is:

1. A device comprising:
a housing assembly defining an inner volume including a cylindrical portion, the housing assembly comprising a first threaded port positioned along a central axis of the device at a first end of the housing assembly and defining a first fluid passage that opens to the inner volume, a second threaded port positioned along the central axis at a second end of the housing assembly and defining a second fluid passage that opens to the inner volume;
a chopper positioned along the central axis within the cylindrical portion, the chopper comprising a first plurality of cutters extending radially relative to the central axis, wherein each cutter of the first plurality of cutters comprises two edges tapered in different directions, and wherein the first plurality of cutters defines a first plurality of apertures;
a first slicer positioned along the central axis within the cylindrical portion, the first slicer abutting the chopper and comprising a second plurality of cutters arranged in a first grid, wherein each cutter of the second plurality of cutters comprises two edges tapered in different directions, wherein the second plurality of cutters defines a second plurality of apertures, wherein each aperture of the second plurality apertures is smaller than each aperture of the first plurality of apertures, and wherein each aperture of the second plurality of apertures has a length between 0.05 mm and 10 mm; and
a second slicer abutting the first slicer, the second slicer comprising a third plurality of cutters arranged in a second grid that is oriented at an acute angle relative to the first grid.

2. The device of claim 1, wherein the housing assembly comprises two housing members.

3. The device of claim 1, wherein the inner volume further includes a frustoconical portion.

4. The device of claim 1, wherein the third plurality of cutters defines a third plurality of apertures, and wherein each aperture of the third plurality of apertures is smaller than each aperture of the second plurality of apertures.

5. The device of claim 4, wherein each aperture of the third plurality of apertures has a length between 0.1 mm and 2.5 mm.

6. The device of claim 1, wherein the chopper comprises a first chopper, and wherein the device further comprises a second chopper positioned along the central axis.

7. The device of claim 6, wherein the first and second slicers are separated by at least one O-ring.

8. The device of claim 7, wherein the at least one O-ring is integral to at least one of the first and second slicers.

9. The device of claim 1, wherein the first and second threaded ports comprise a Luer lock mating pair member.

* * * * *